United States Patent [19]
Kantor et al.

[11] Patent Number: 4,753,798
[45] Date of Patent: Jun. 28, 1988

[54] METHODS AND COMPOSITIONS FOR CONTROLLING PROTOZOAL INFECTIONS IN WARM-BLOODED ANIMALS

[75] Inventors: Sidney Kantor, Cranbury; Robert L. Kennett, Jr., Lambertville, both of N.J.

[73] Assignee: American Cyanamid Company, Stamford, Conn.

[21] Appl. No.: 880,229

[22] Filed: Jun. 30, 1986

[51] Int. Cl.$^4$ ............................................. A61K 35/00
[52] U.S. Cl. ................................... 424/122; 424/116
[58] Field of Search .............................. 424/116, 122

[56] References Cited

U.S. PATENT DOCUMENTS 4,148,890  4/1979  Czok et al. ........................... 424/116

Primary Examiner—Frederick E. Waddell
Attorney, Agent, or Firm—Alice C. Brennan

[57] ABSTRACT

This invention relates to methods and compositions for the control of protozoal infections in warm-blooded animals by administering to said animals a protozoacidally-effective amount of a new antibiotic designated LL-E19020α, LL-E19020β or a pharmaceutically and prophylactically acceptable salt thereof. The new antibiotics are produced by microbiological fermentation under controlled conditions using a new strain of *Streptomyces lydicus* subspecies tanzanius or mutants thereof.

7 Claims, 9 Drawing Sheets

METHODS AND COMPOSITIONS FOR CONTROLLING PROTOZOAL INFECTIONS IN WARM-BLOODED ANIMALS

BACKGROUND OF THE INVENTION

Protozoan parasites are known to infect both man and animals and to have exceedingly debilitating effects there upon.

Although the art is replete with reports of diseases stemming from protozoal infections, coccidiosis, malaria and babesia, are, perhaps, the most commonly encountered diseases resulting from protozoan infections in animals and/or man. Coccidiosis is an extremely severe disease that frequently afflicts swine, poultry, such as chickens, turkeys and geese, and ruminants such as cattle and sheep. This disease can strike with devastating suddenness and destroy an entire flock of birds or decimate a herd of cattle or flock of sheep or it may manifest itself as a mild outbreak that simply causes weight loss of the infected animals and reduces efficiency of feed utilization thereby. However, regardless of the manner in which the disease afflicts the host animals, significant monetary losses generally accompany such disease outbreaks when they occur in flocks or herds of meat producing or companion animals.

The protozoan parasites usually responsible for coccidiosis in the above-mentioned animals are generally of the genus Eimeria. Six species which have been shown to be primary causive agents for the disease are: *Eimeria tenella, Eimeria necatrix, Eimeria mivati, Eimeria maxima, Eimeria brunetti* and *Eimeria acervulina*. In swine it has been shown that the protozoan *Isospora suis* is also responsible for coccidiosis.

Babesia infections, like Eimeria infections, have been a major concern to the livestock industry for many years. These infections frequently produce anemia and death in the infected animals and are responsible for significant economic losses for the livestock producers. While Babesia infections have generally been found to occur in ruminants, in recent years it has been discovered that the disease is also transmitted to domesticated pets such as dogs and to humans.

Importantly, it has been recognized by the livestock industry that there is no entirely satisfactory method for preventing, treating or controlling, Babesia infections in livestock, domestic animals or humans, presently available.

It is therefore an object of the present invention to provide a method for preventing, treating or controlling Babesia infections in warm-blooded animals.

It is also an object of this invention to provide a method for preventing, treating or controlling coccidiosis in warm-blooded animals.

Anticoccidial treatments that have met with some success and acceptance by the poultry industry include the anticoccidial treatments of E. Waletzky et al. described in Reissue U.S. Pat. No. Re. 26,833 reissued Mar. 24, 1970; the A. S. Tomcufcik, U.S. Pat. No. 3,769,432 issued Oct. 30, 1973 and the W. D. Celmer et al. U.S. Pat. No. 4,148,882, issued Apr. 10, 1979. The drugs described in these patents are useful for treating coccidial infections in poultry; but, new more effective treatments are needed if the industry is to successfully control the disease that plagues meat production throughout the world.

It is, therefore, another object of the present invention to provide a novel method for preventing, treating or controlling, protozoan infections in warm-blooded animals.

SUMMARY OF THE INVENTION

The present invention relates to methods and compositions effective for preventing, treating, controlling or ameliorating, protozoal infections in warm-blooded animals, particularly in poultry, cattle, sheep swine and goats and in companion animals such as dogs and rabbits.

The antibiotics which are effective when used in the compositions and methods of the present invention are antibiotics LL-E19020α, LL-E19020β and the pharmaceutically and pharmacologically acceptable salts of said antibiotics. These antibiotics LL-E19020α and LL-E19020β and a method for the preparation thereof are described in the application of G. T. Carter; M. Greenstein; J. J. Goodman; D. B. Borders; W. M. Maiese and R. T. Testa; which issued under U.S. Pat. No. 4,705,688 on Nov. 10, 1987 and which is incorporated herein by reference thereto.

The above-said antibiotics and the pharmaceutically and prophylactically acceptable salts thereof are effective for preventing or controlling protozoal infections in said warm-blooded animals, when administered to said animals in protozoacidally effective amounts. More particularly, said antibiotics and antibiotic salts are especially effective for treating, preventing, controlling or ameliorating protozoal infections in swine, poultry, ruminants and companion animals.

The above antibiotics are also effective for controlling protozoan infections caused by Eimeria and Babesia species in cattle, sheep, swine, chickens, turkeys, ducks, geese and dogs.

It is also anticipated that the antibiotic compositions of this invention will prove to be effective for controlling malaria, sarcosporidiosis and toxoplasmosis in warm-blooded animals since the causative agents for these diseases are protozoan infections biologically related to Eimeria and Babesia.

BRIEF DESCRIPTION OF THE DRAWINGS

FIG. I shows an ultraviolet absorption spectra of LL-E19020α.

FIG. II shows an infrared absorption spectrum of LL-E19020α.

Figure 1:
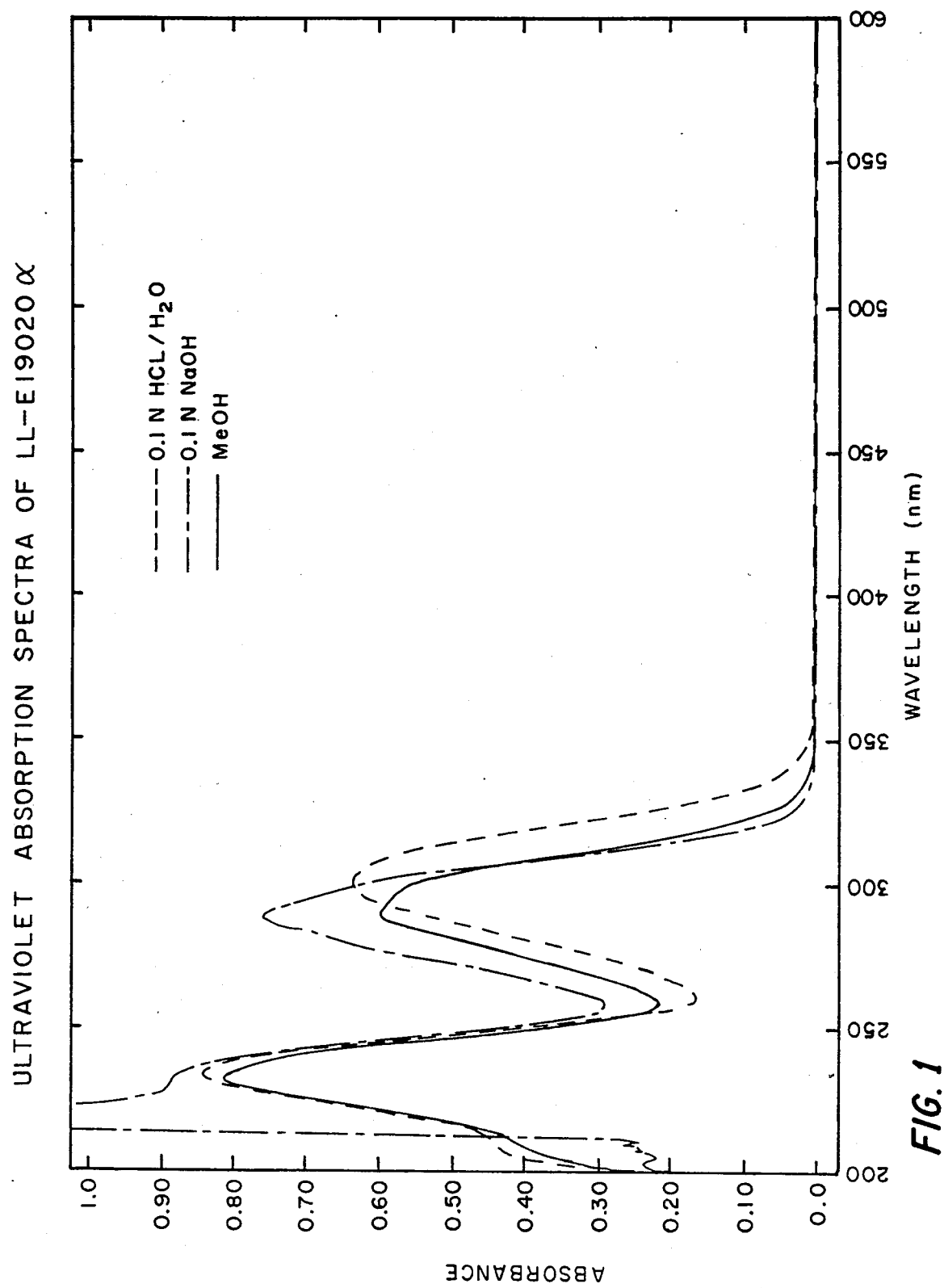
Figure 2:
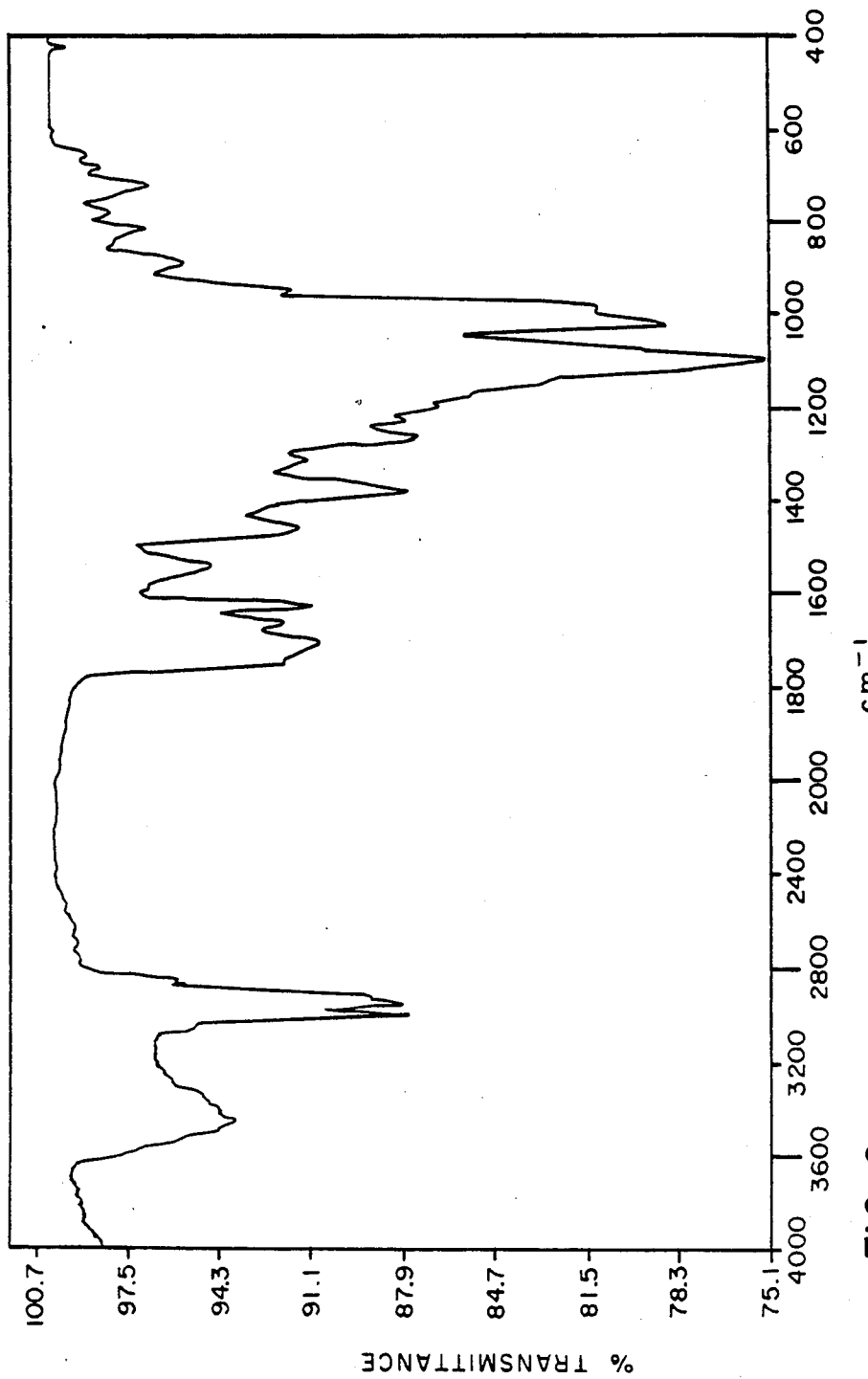
Figure 3:
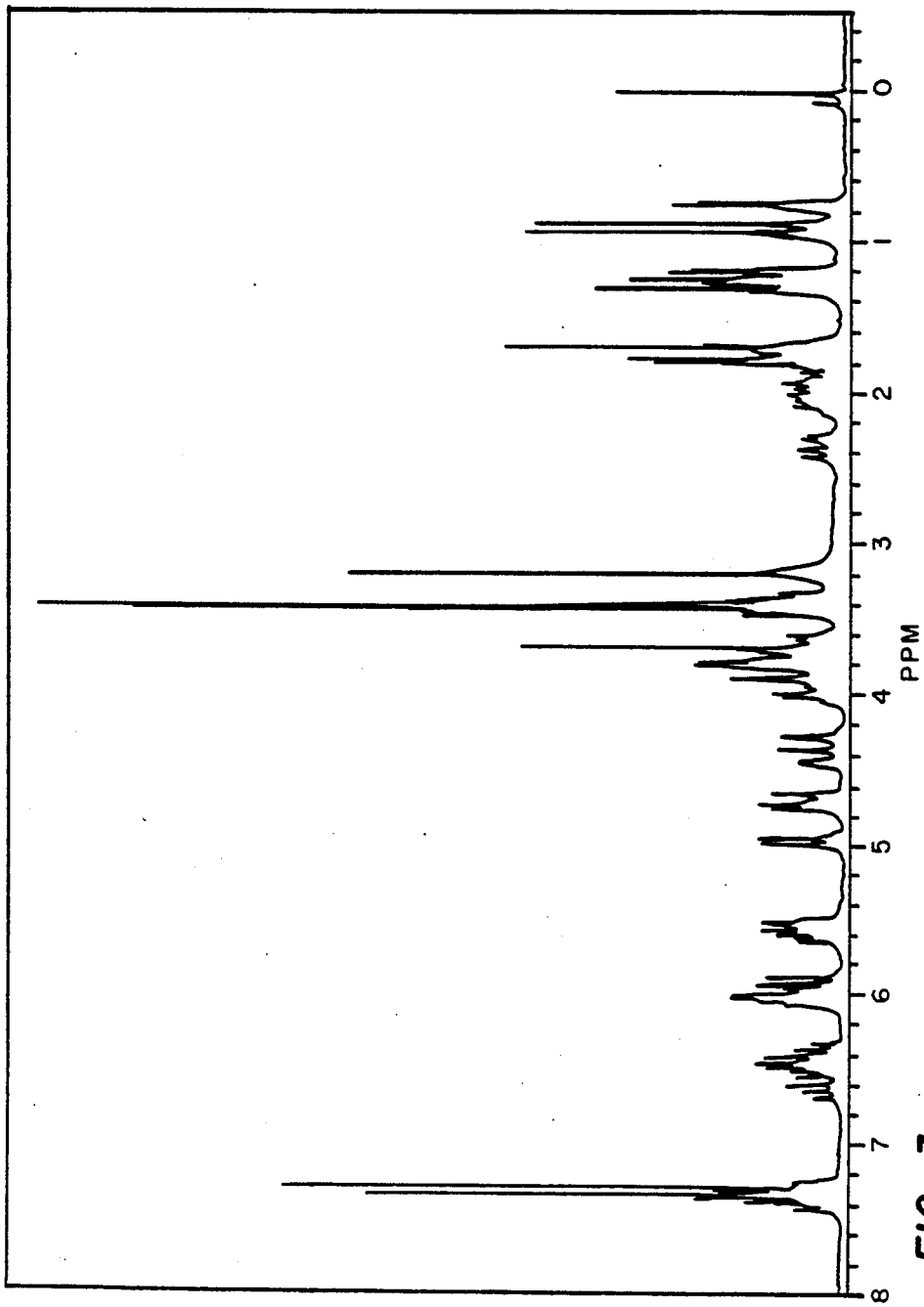
Figure 4:
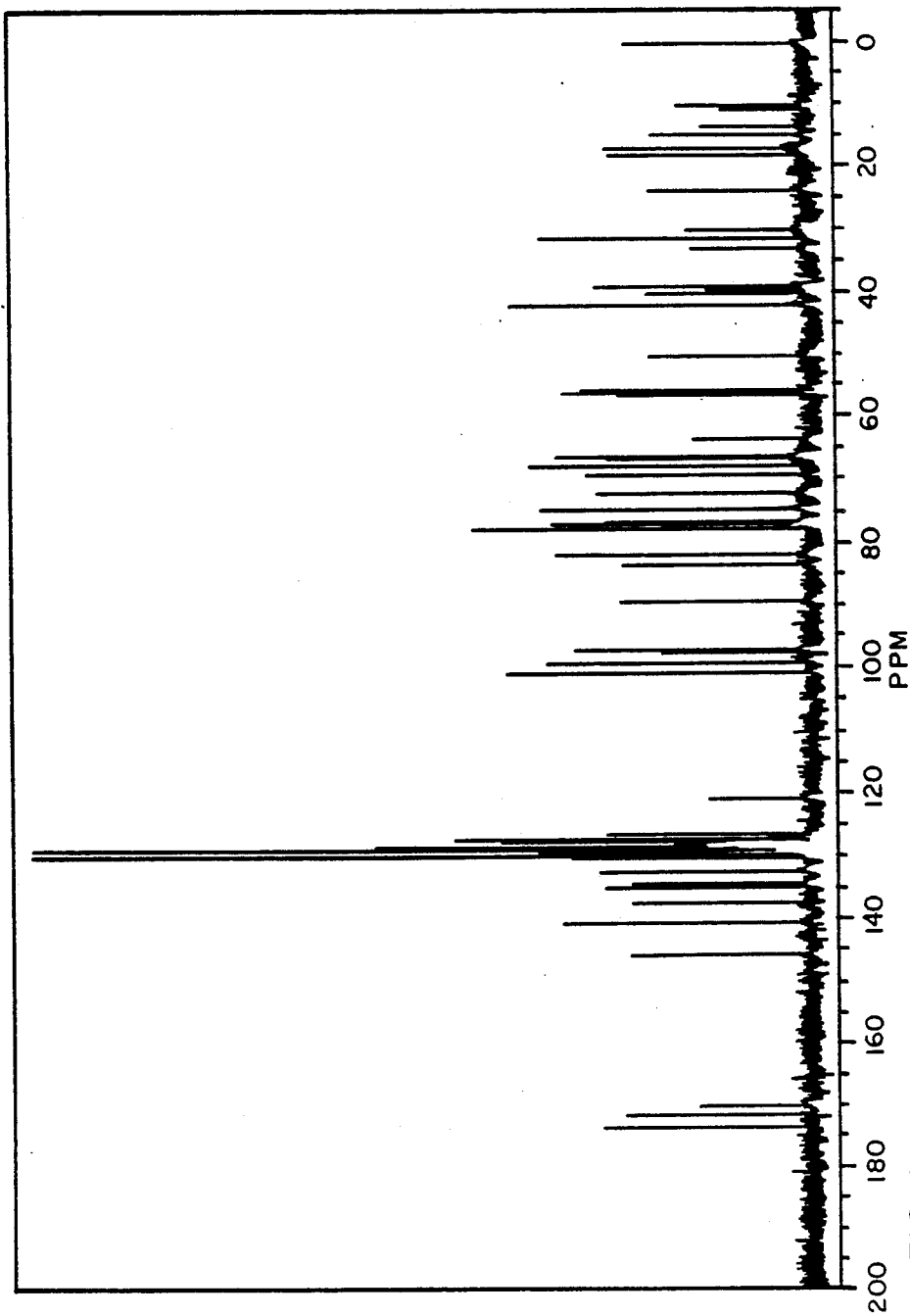
Figure 5:
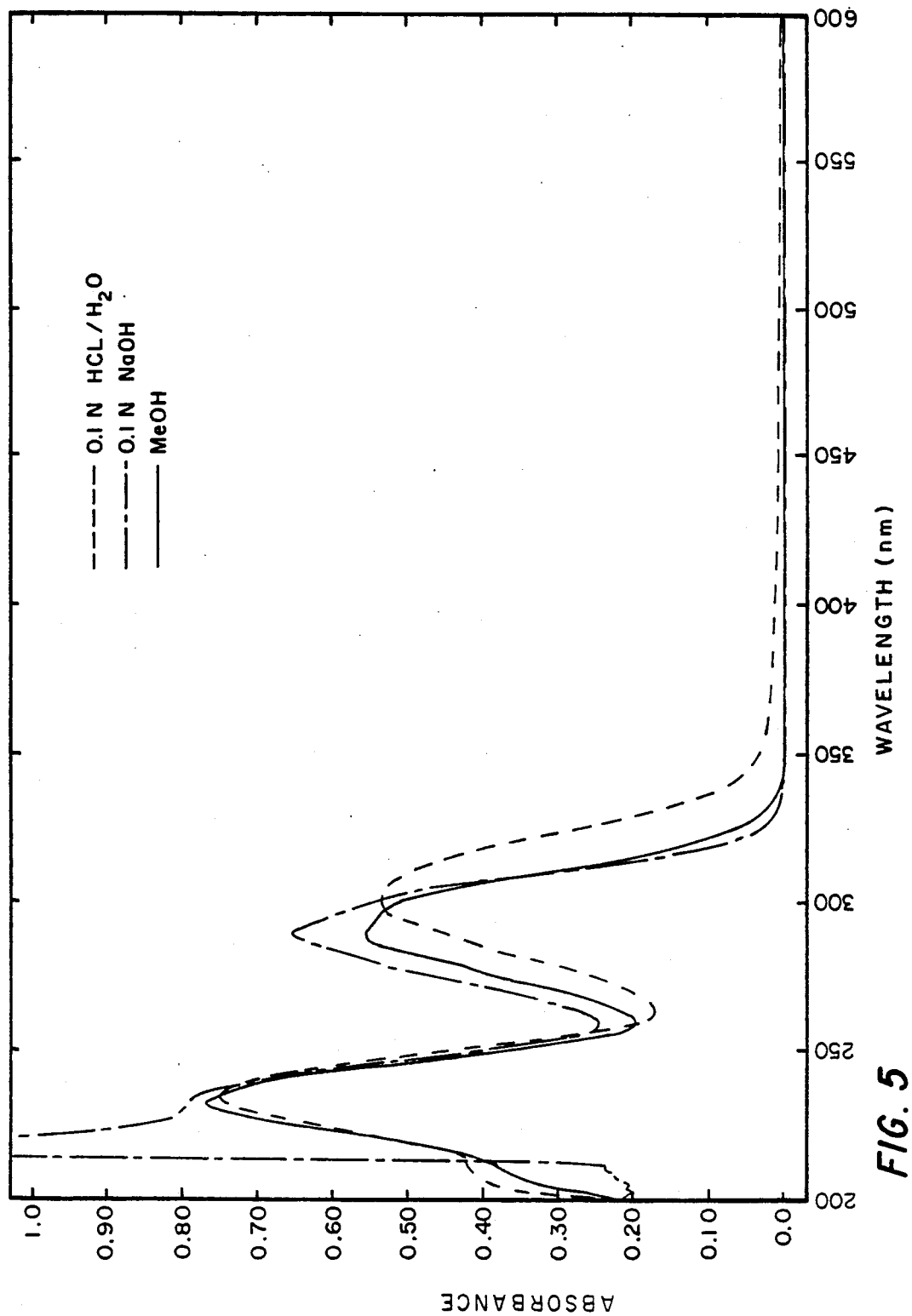
Figure 6:
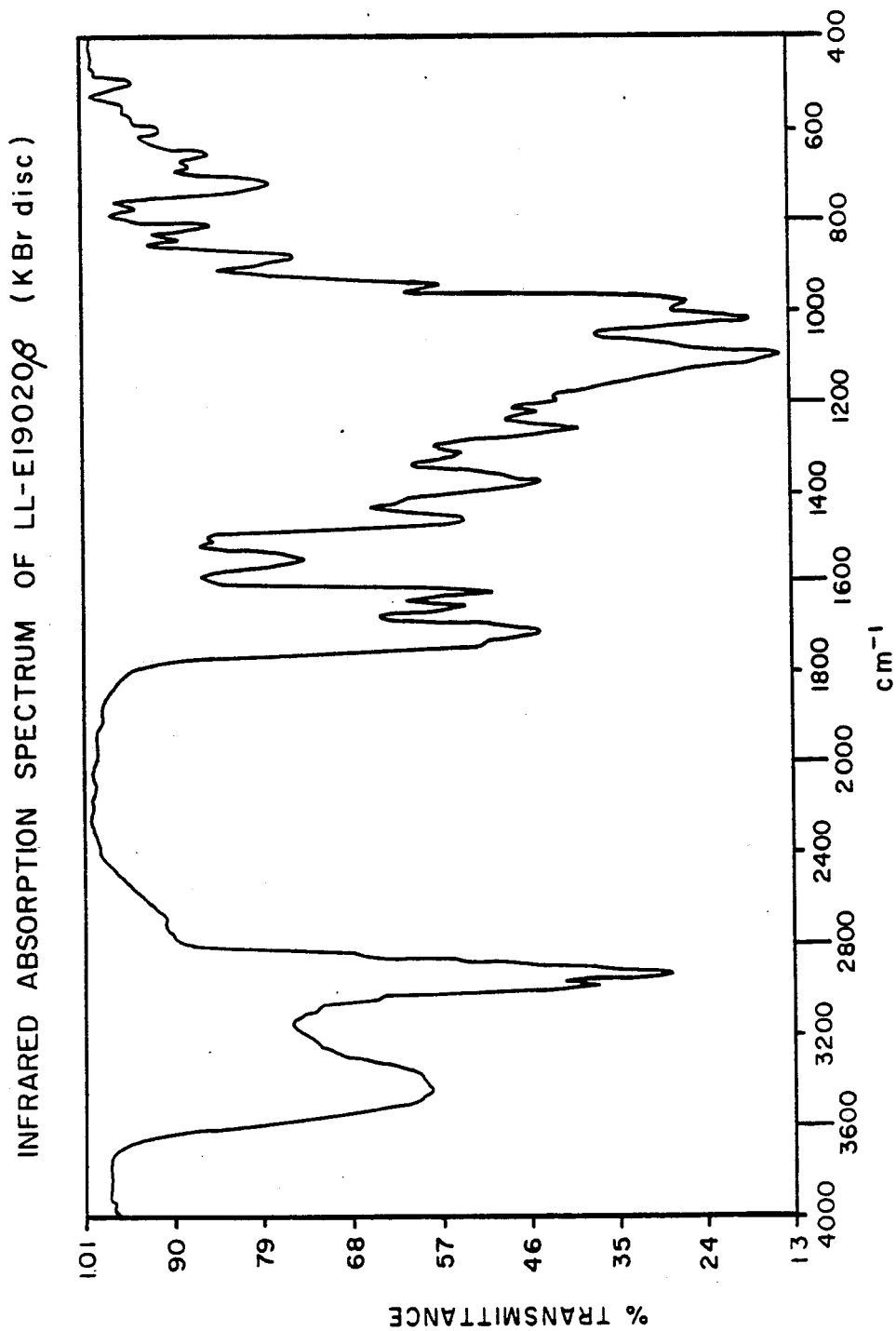
Figure 7:
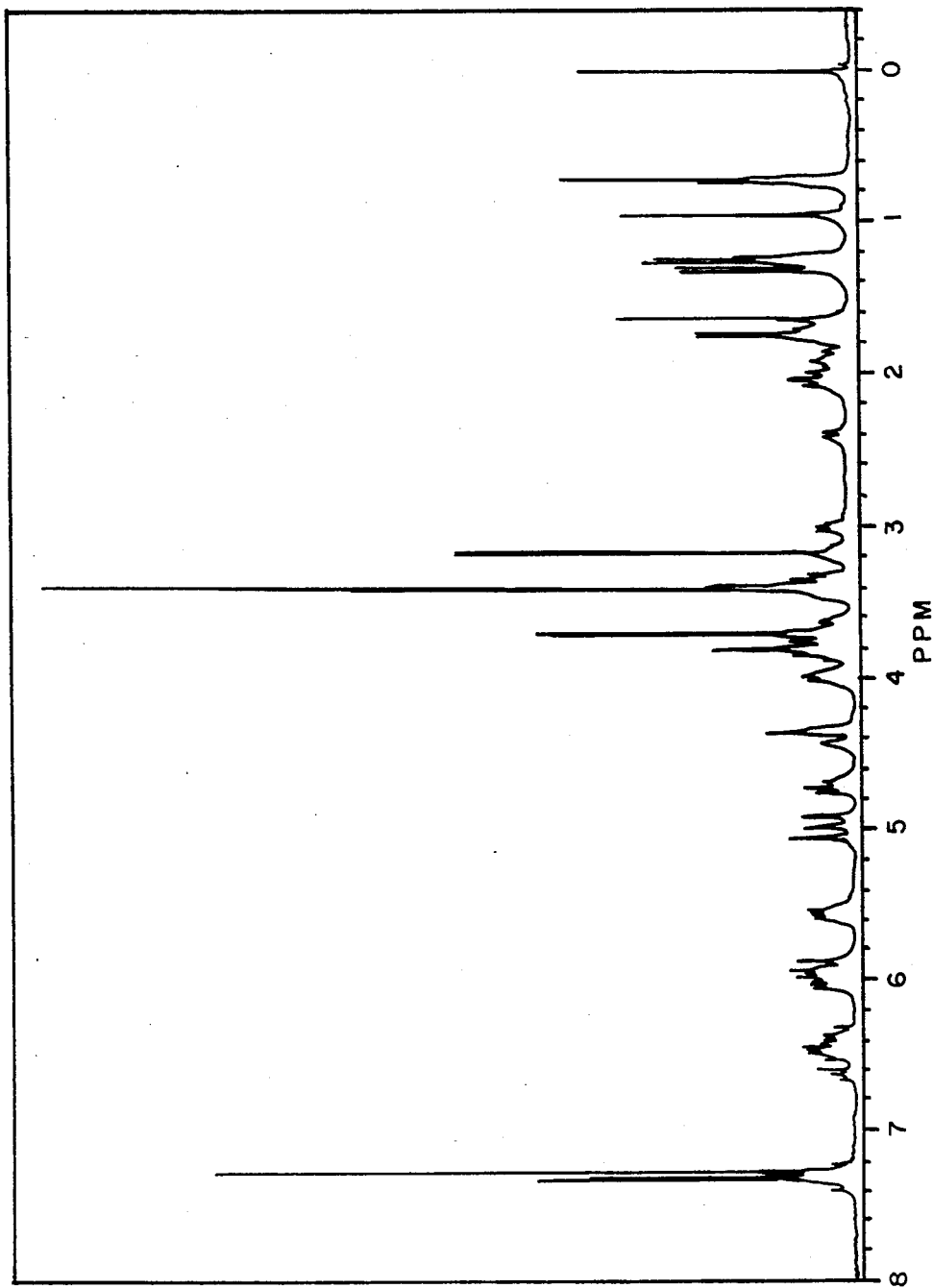
Figure 8:
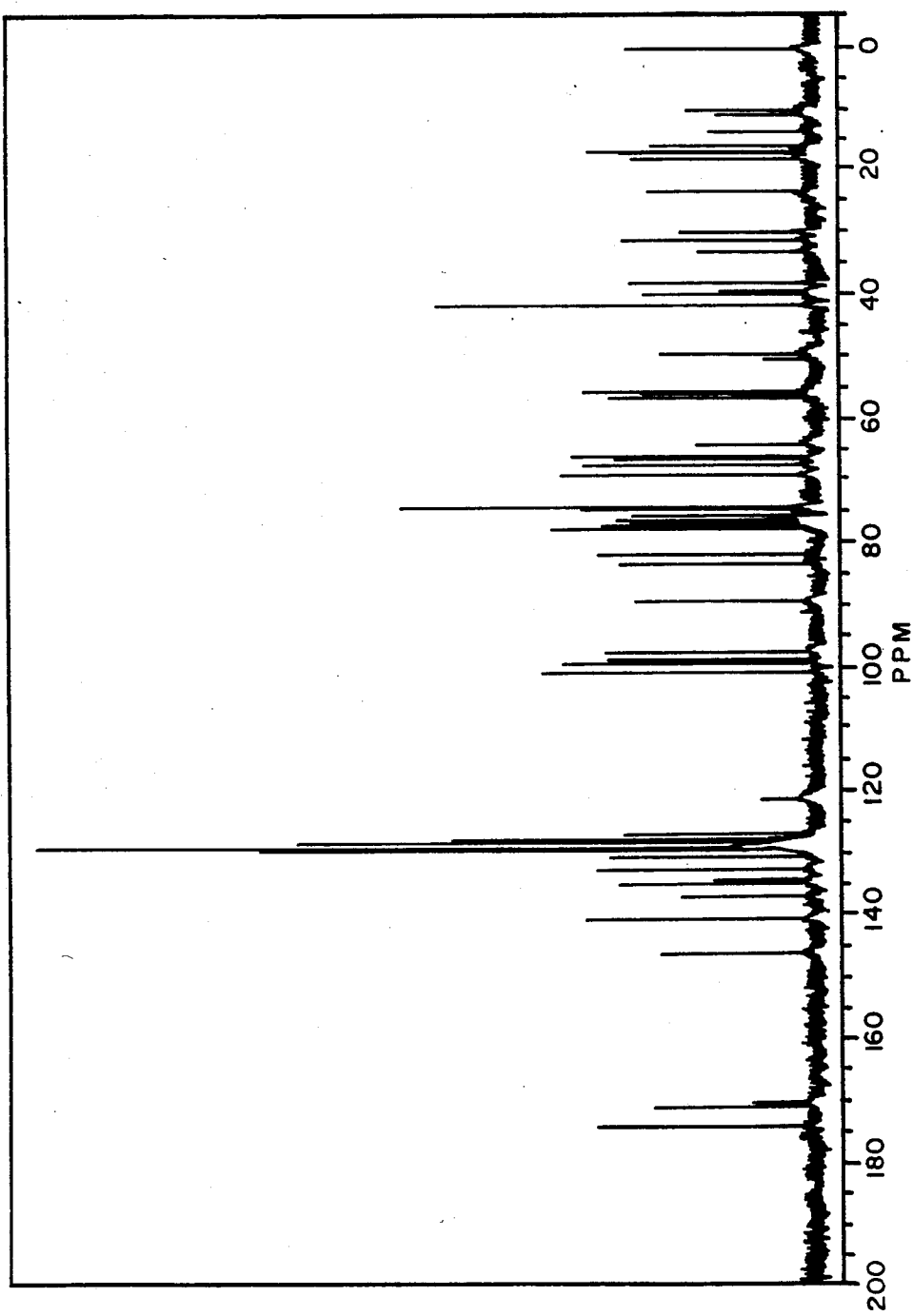
Figure 9:
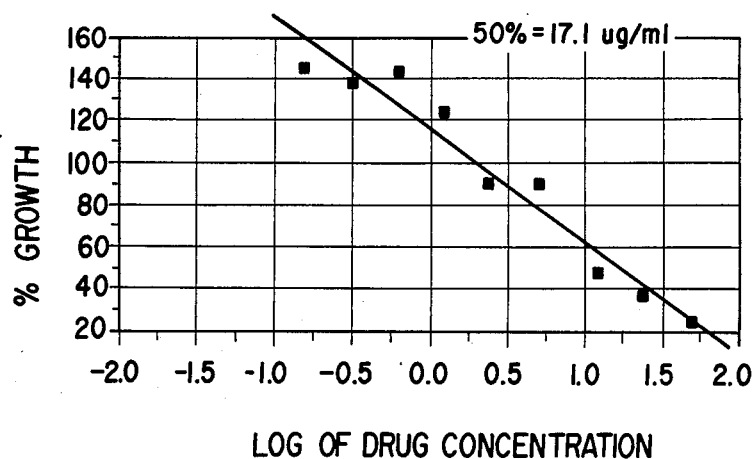

FIG. III shows a proton nuclear magnetic resonance spectrum of LL-E19020α.

FIG. IV shows a carbon-13 nuclear magnetic resonance spectrum of LL-E19020α.

FIG. V shows an ultraviolet absorption spectra of LL-E19020β.

FIG. VI shows an infrared absorption spectrum of LL-E19020β.

Fig VII shows a proton nuclear magnetic resonance spectrum of LL-E19020β.

FIG. VIII shows a carbon-13 nuclear magnetic resonance spectrum of LL-E19020β.

FIG. IX shows the effect of LL-E19020α on the growth of *B. bigemina*.

DESCRIPTION OF THE PREFERRED EMBODIMENTS

Administration of the above-identified antibiotics for control, treatment or prevention of protozoan infections in meat-producing and companion animals, will generally be most practical in or with the feed or drinking water of the animals. However, said antibiotics can be given to the animals on an individual basis in the form of capsules, tablets, oral gels, or the like. They may also be administered parenterally, generally by subcutaneous injection, as a gel, paste, pellet, solution or the like, under the skin of the host animal.

In the practice of the present invention the antibiotics LL-E19020α, LL-E19020β and the pharmaceutically and pharmacologically acceptable salts thereof, may be employed prophylactically, pharmaceutically or therapeutically for the control, prevention or inhibition of protozoal infections in poultry and ruminants. Generally about 0.1 ppm to 300 ppm, and preferably about 1 to 100 ppm of the antibiotic or antibiotic salt, in feed or drinking water, is effective for controlling protozoal infections, such as coccidiosis and Babesia in poultry, ruminants and companion animals.

Medicated animal feeds useful in the method of the present invention are usually prepared by thoroughly admixing about 0.00001% by weight to 0.03% by weight of the antibiotic LL-E19020α or β or salt thereof with a nutritionally balanced daily ration.

When using the compound of the invention for the prevention or control of protozoal infections, the active antiprotozoal agent is generally first prepared as an animal feed premix. The premix usually contains a relatively high percentage of the antiprotozoal agent and is generally blended with the animal's feed just prior to administration. If desired, the feed premix may also be applied as a top dressing for the animal's daily ration.

Feed premixes or concentrates, useful in the practice of the present invention may be prepared by admixing about 1.0 to 15.0% by weight of the above-identified antibiotic, or a pharmaceutically and pharmacologically acceptable salt thereof, with about 99.0% to 85% by weight of a suitable carrier or diluent. Carriers suitable for use to make up the feed supplement compositions include the following: alfalfa meal, soybean meal, cottonseed oil meal, linseed oil meal, sodium chloride, calcium carbonate, corn meal, cane molasses, urea, bone meal, corncob meal, rice hull meal, and the like. The carrier promotes an essentially uniform distribution of the active ingredient in the finished feed into which the supplement is blended. It thus performs an important function by ensuring proper distribution of the active ingredient throughout the feed.

In practice, usually one or more pounds of premix is added per ton of feed to obtain the desired level of antibiotic in the finished feed.

If the supplement or premix is used as a top dressing for feed, it likewise helps to ensure uniformity of distribution of the active material across the top of the dressed feed.

Since the compound of this invention and its pharmaceutically and pharmacologically acceptable salts are relatively insoluble in water, it is generally desirable, when administering the compound in the animal's drinking water, to dissolve the active compound in an organic solvent such as methanol, ethanol, acetone, DMSO, oleic acid, linoleic acid, propylene glycol, or the like, and admix with the solution a small amount of surfactant and/or dispersing agent to assure solution and/or dispersion of the active ingredient in the animal's drinking water.

When administered to cattle, sheep, swine, poultry or companion animals on a mg/kg of body weight/day basis, generally about 0.0001 to 15 mg/kg of animal body weight per day, is effective for preventing or controlling protozoan infections in the above said animals. For prolonged treatment of animals, rates of from about 0.0001 mg/kg body weight/day to 5 mg/kg of animal body weight/day are usually employed.

For parenteral administration, the antibiotic or antibiotic salt may be prepared in the form of a paste or pellet and administered as an implant, usually under the skin or the head or ear of the animal.

In practice, parenteral administration generally involves injection of a sufficient amount of the above said antibiotic or antibiotic salt to provide the animal with from about 0.0001 to 15 mg/kg of body weight of the active ingredient.

Paste formulations can be prepared by dispersing the antibiotic or antibiotic salt in a pharmaceutically acceptable oil such as peanut oil, sesame oil, corn oil or the like.

Pellets containing an effective level of the antibiotic LL-E19020α or LL-E19020β can be prepared by admixing the above-said antibiotic with a diluent, such as carbowax, biodegradable polymers, carnauba wax, or the like. A lubricant, such as magnesium stearate or calcium stearate may be added to improve the pelleting process if desired.

It is, of course, recognized that more than one pellet may be administered to an animal to achieve the desired dose level which will provide the increased growth rate and/or improve efficiency of feed utilization by said animal. Moreover, it has been found that additional implants may also be introduced periodically during the treatment period in order to maintain the proper drug release rate in the animal's body.

The antibiotics of this invention, LL-E19020α and LL-E19020β, are formed during the cultivation under controlled conditions of a new strain of *Streptomyces lydicus* ssp. *tanzanius*.

This microorganism is maintained in the culture collection of the Medical Research Division, American Cyanamid Company, Pearl River, N.Y. as culture number LL-E19020. A viable culture of this new microorganism has been deposited with the Patent Culture Collection Laboratory, Northern Regional Research Center, U.S. Department of Agriculture, Peoria, Ill. 61604, and has been added to its permanent collection. It has been assigned the strain designation NRRL 18036 by said depository. Access to said culture, under strain designation NRRL 18036, during pendency of the instant application shall be available to one determined by the Commissioner of Patents and Trademarks to be entitled thereto under 37 C.F.R. §1.14 and 35 U.S.C. §122, and all restrictions on availability to the public of such culture will be irrevocably removed upon grant of a patent on the instant application.

Culture LL-E19020 produces short spiral spore chains, 10–50 spores long, with occasional longer chains. These tend to coalesce to form dry blackish masses on such ISP media as oatmeal and inorganic salts-starch. The spores have smooth surfaces as assessed by electron microscopy. The strain contains the L isomer of diaminopimelic acid, and may thus be assigned to the genus Streptomyces.

In the ISP tests for utilization of carbohydrates, LL-E19020 shows growth on arabinose, fructose, inositol, mannitol, raffinose, rhamnose, sucrose and xylose. Cellulose is not utilized.

The reaction of LL-E19020 in the Gordon physiological series are compared in Table I with those of *Strepto-*

*myces lydicus* ISP 5461 which it most closely resembles morphologically and physiologically.

Because LL-E19020 differs from ISP 5461 in five characteristics (xanthine hydrolysis, decarboxylation of oxalate, acid from erythritol, rhamnose and β-methyl-D-xyloside) it is designated as a subspecies of *Streptomyces lydicus*.

TABLE I

Gordon Test Reactions of LL-E19020 and *Streptomyces lydicus* ISP 5461

| Reaction | LL-E19020 | ISP 5461 |
|---|---|---|
| Degradation/Transformation of | | |
| Casein | + | + |
| Xanthine | − | + |
| Hypoxanthine | + | + |
| Tyrosine | + | + |
| Adenine | + | + |
| Production of | | |
| Amylase | + | + |
| Gelatinase | + | + |
| Phosphatase | + | + |
| Nitrate Reductase | − | − |
| Urease | + | + |
| Exculinase | + | + |
| Growth on/in | | |
| 5% Sodium chloride | + | + |
| Salicylate | − | − |
| Lysozyme Broth | trace | trace |
| Utilization | | |
| Acetate | + | + |
| Benzoate | − | − |
| Citrate | + | + |
| Lactate | + | + |
| Malate | + | + |
| Mucate | + | + |
| Oxalate | + | − |
| Propionate | + | + |
| Pyruvate | + | + |
| Succinate | + | + |
| Tartrate | − | − |
| Growth at | | |
| 10° C. | + | + |
| 42° C. | − | − |
| 50° C. | − | − |
| Acid from | | |
| Adonitol | + | + |
| Arabinose | + | + |
| Cellobiose | + | + |
| Dextrin | + | + |
| Dulcitol | − | − |
| Erythritol | + | − |
| Fructose | + | + |
| Galactose | + | + |
| Glucose | + | + |
| Glycerol | + | + |
| Inositol | + | + |
| Lactose | + | + |
| Maltose | + | + |
| Mannitol | + | + |
| Mannose | + | + |
| Melibiose | + | + |
| α-Methyl-D-Glucoside | + | + |
| Raffinose | + | + |
| Rhamnose | + | − |
| Salicin | + | + |
| Sorbitol | + | + |
| Sucrose | + | + |
| Trehalose | + | + |
| Xylose | + | + |
| β-Methyl-D-Xyloside | + | − |

It is to be understood that for the production of these new antibacterial agents the present invention is not limited to this particular organism or to organisms fully answering the above characteristics which are given for illustrative purposes only. In fact, it is desired and intended to include the use of mutants produced from this organism by various means such as exposure to X-radiation, ultraviolet radiation, N'-nitro-N-nitrosoguanidine, actinophages and the like.

General Fermentation Conditions

Cultivation of *Streptomyces lydicus* ssp. *tanzanius* NRRL 18036 may be carried out in a wide variety of liquid culture media. Media which are useful for the production of LL-E19020α and LL-E19020β include an assimilable source of carbon, such as dextrin, sucrose, molasses, glycerol, etc.; an assimilable source of nitrogen such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicon oil may be added as needed.

General Procedure for the Isolation of LL-E19020α and LL-E19020β

The LL-E19020α and LL-E19020β antibiotics are recovered from the fermentation broth by pH adjustment to 4.5–5.5, filtration through diatomaceous earth, extraction into a solvent such as ethyl acetate, concentration, dissolution in a solvent such as dichloromethane and purification by column chromatography on silica gel using successively, dichloromethane and methanol:-dichloromethane (1:4), giving a crude product.

The crude product is then separated into the α and β components and further purified by high performance liquid chromatography on a reverse-phase column using the system acetonitrile, 0.1 M ammonium acetate buffer pH 4.3 (1:1).

The physico-chemical characteristics of LL-E19020α are as follows:

LL-E19020α

1. Approximate elemental analysis: C 62.73; H 7.60; N 1.00; O 28.67 (by difference);
2. Molecular weight: 1225 (FABMS);
3. Apparent molecular formula: $C_{64}H_{91}NO_{22}$;
4. Specific rotation: $[\alpha]_D^{26} = 0$ (C 0.385, methanol);
5. Ultraviolet absorption spectra: as shown in FIG. I $$UV_{MAX}^{CH_3OH} = \begin{array}{l} 233nm\ (\epsilon\ 49{,}800) \\ 290nm\ (\epsilon\ 36{,}600) \end{array}$$

6. Infrared absorption spectrum: as shown in FIG. II (KBr disc): 3420, 2970, 2925, 1717, 1695, 1647, 1617, 1525, 1445, 1365, 1092, 1018 cm$^{-1}$;
7. Proton nuclear magnetic resonance spectrum: as shown in FIG. III (300 MHz, CDCl$_3$);
8. Carbon-13 nuclear magnetic resonance spectrum: as shown in FIG. IV (75 MHz, CDCl$_3$, ppm downfield from TMS), significant peaks as below:

| | | | | | |
|---|---|---|---|---|---|
| 173.3 | 129.0 | 97.3 | 74.2 | 55.4 | 17.2 |
| 171.4 | 128.6(2x) | 97.0 | 72.0 | 49.8 | 17.0 |
| 170.1 | 128.43 | 89.2 | 71.9 | 41.8 | 14.8 |
| 145.7 | 128.38 | 83.3 | 69.1 | 39.8 | 13.5 |
| 140.3 | 128.1(2x) | 81.6 | 67.5 | 39.1 | 10.8 |
| 137.0 | 127.5 | 77.6 | 66.4 | 38.8 | 10.0 |
| 134.4 | 127.1 | 77.0 | 66.1 | 32.9 | |

-continued

| | | | | |
|---|---|---|---|---|
| 133.9 | 126.3 | 76.4 | 63.5 | 31.0 |
| 132.0 | 120.8 | 74.6 | 56.5 | 29.9 |
| 130.1 | 100.6 | 74.5 | 56.0 | 23.8 |
| 129.5(2x) | 99.0 | 74.4 | 55.6 | 18.1 |

2x = two overlapping signals

LL-E19020β

1. Approximate elemental analysis: C 63.33; H 7.72; N 1.16; O 27.79 (by difference);
2. Molecular weight: 1225 (FABMS);
3. Apparent molecular formula: $C_{64}H_{91}NO_{22}$;
4. Specific rotation: $[\alpha]_D^{26} = -17 \pm 2$(C 0.455, methanol);
5. Ultraviolet absorption spectra: as shown in FIG. V $$UV_{MAX}^{CH_3OH} = \begin{matrix} 233\text{nm} (\epsilon\ 47,000) \\ 290\text{nm} (\epsilon\ 34,100) \end{matrix}$$

$$UV_{MAX}^{0.1N\ HCl} = \begin{matrix} 234\text{nm} (\epsilon\ 46,000) \\ 301\text{nm} (\epsilon\ 32,800) \end{matrix}$$

$$UV_{MAX}^{0.1N\ NaOH} = \begin{matrix} 217\text{nm} (\epsilon\ 77,800) \\ 290\text{nm} (\epsilon\ 39,700) \end{matrix}$$

6. Infrared absorption spectrum: as shown in FIG. VI (KBr disc): 3430, 2970, 2930, 1712, 1648, 1620, 1543, 1454, 1367, 1265, 1098, 1020, 980 cm$^{-1}$;
7. Proton nuclear magnetic resonance spectrum: as shown in FIG. VII (300 MHZ, CDCl$_3$);
8. Carbon-13 nuclear magnetic resonance spectrum, as shown in FIG. VIII (75 MHz, CDCl$_3$, ppm downfield TMS), significant peaks as listed below.

| | | |
|---|---|---|
| 173.6 | 99.0 | 55.4 |
| 170.6 | 98.4 | 49.6 |
| 170.0 | 97.2 | 41.6(2x) |
| 145.6 | 89.2 | 39.8 |
| 140.2 | 83.3 | 39.1 |
| 136.7 | 81.6 | 38.0 |
| 134.4 | 77.6 | 32.9 |
| 133.9 | 77.5 | 31.1 |
| 132.0 | 76.2 | 29.9 |
| 130.1 | 75.5 | 23.7 |
| 129.1(2x) | 74.6 | 18.1 |
| 128.9 | 74.5 | 17.2 |
| 128.6(2x) | 74.2 | 17.0 |
| 128.5 | 69.1 | 16.2 |
| 128.4 | 68.9 | 13.5 |
| 128.3 | 67.5 | 10.8 |
| 128.2 | 66.6 | 10.0 |
| 127.8 | 66.1 | |
| 127.2 | 64.1 | |
| 126.5 | 56.5 | |
| 120.9 | 56.0 | |
| 100.6 | 55.6 | |

2x = two overlapping signals

EXAMPLE 1

Evaluation of test compounds as anticoccidial agents-*Eimeria tenella*

Anticoccidial Cell Culture Screen (*E. tenella*)

Monolayers are initiated from primary kidney cells obtained from 7 day old chickens. Generally, 50,000 cells are administered in 1 mL volumes of culture medium into 24 well cluster plates. The medium of preference is M199 buffered with 0.125% NaHCO$_3$. 5% fetal bovine serum is added to complete the medium.

Monolayers are permitted to grow to 50% confluency prior to inoculation and drug medication. This usually requires 48 hours in a humidified incubator held at 41° C. in an atmosphere of 5% CO$_2$--95% air.

Inocula containing 60,000 *E. tenella* sporozoites per 1 mL (2 mL total volume) is utilized to infect adequately confluent monolayers. Initial medium is aspirated off prior to administering 1.9 mL of sporozoite containing maintenance medium.

Medication is administered at predetermined concentrations in 0.1 mL volumes immediately after the introduction of sporozoites. As a rule synthetic compounds are tested at 1 ppm and crude fermentation products at a dilution of 1:200. The former are dissolved in DMSO and the latter in phosphate buffered saline. Penicillin and streptomycin are added to all medium to control possible contamination.

Treatments are observed by inverted phase contrast microscopy at 96-120 hours post-inoculation for cytotoxicity and anticoccidial activity. No staining of monolayers is required. Agents which prevent or markedly reduce the development of second generation asexual stages of the parasite life cycle are considered active. Medications which prevent an anticoccidial reading due to gross cytotoxicity are diluted 2 fold until endpoints are achieved. Actives are generally diluted to inactivity to determine relative potency.

Monensin and robenidine are included in all experiments as positive standards. Data obtained are reported in Table 2 below.

TABLE 2

Evaluation of Test Compounds Using In Vitro Anticoccidial Screen - *Eimeria tenella*

| Compound | Results in ppm of Culture Medium | | | | | |
|---|---|---|---|---|---|---|
| | 5 | 2.5 | 1.25 | 0.6 | 0.3 | 0.15 |
| LL-E19020α | T | T | A | A | a | O |
| LL-E19020β | T | T | T | T | A | A |

Performance Rating
T = Toxic
A = Active
a = Marginal Activity
O = Inactive

EXAMPLE 2

Evaluation of test compounds as anticoccidial agents *Eimeria mitis*

Anticoccidial Embryonated Egg Assay-*E. mitis*

Chick embryos which are 10 days of age are candled for viability and placed into groups of 5 eggs each. A small hole is punched into the chorioallantoic cavity as an avenue for chemical agents. Synthetic compounds are screened at 1 mg per embryo and crude natural products at 0.2 mL per embryo. Penicillin/streptomycin is utilized to control contamination. After administration of drugs via sterile tuberculin syringe, the pin hole is sealed with collodion. The embryos are returned to a humidified incubator set at 103° F. and held for 24 hours. All embryos are then recandled to remove any dead due to toxicity of drug treatment. All surviving embryos are then inoculated through the original pin hole with 80,000 *E. mitis* sporozoites in a volume of 0.1 mL. Embryos are resealed and returned to the incubator. After 6 days all embryos are again candled and the dead removed and recorded. The chorioallantoic (CAM) membranes from each treatment are pooled and homogenized in 50–70 mL of tap water. Oocyst counts are then performed with a hemocytometer. A treatment is considered active if there is a 80% or greater reduction of oocysts compared to the numbers detected in the 4 replicates of nonmedicated inoculated controls. Two or more embryos must survive for a valid anticoccidial reading. In groups where one or no eggs remain after 6 days two fold dilutions are performed until an anticoccidial reading can be realized. Robenidine is used as a positive drug at 0.1 mg per embryo.

The *E. mitis* utilized has been made adaptable to this assay through repeated passages in embryos. (P. L. Long).

Data obtained are reported in Table 3 below.

TABLE 3

Evaluation of Test Compounds as Anticoccidial Agents - *Eimeria mitis*

| Compound | Milligrams of Drug Per Embryo | | |
|---|---|---|---|
| | 1 | 0.5 | 0.25 |
| LL-E19020α | A | A | O |
| LL-E19020β | O | | |

Performance Rating
T = Toxic
A = Active
a = Marginal Activity
O = Inactive

EXAMPLE 3

Evaluation of test compounds for controlling *Babesia bovis* and *Babesia bigemina*

For these evaluations laboratory cultures of *Babesia bovis* and *Babesia bigemina* are continuously maintained. A normal donor animal is maintained as a source of normal RBC's and serum.

Babesia cultures are maintained as follows:
1. The percent of Babesia growing in each flask is determined. If the percent is under 10% the cultures are fed.
2. When the percent of Babesia in a flask is between 10–20% and the cells and Babesia look healthy the culture should be split or used for the drug screening.

A.

Media for Babesia cultures
30 mL 199(Earls) Media
20 mL serum
1 mL TES
Check pH (7.00) and adjust if necessary
Filter sterilize

B.

Feeding of Babesia cultures
Always put exactly the same amount of media in a culture as you remove.

C.

Splitting Babesia cultures
Remove media from flask but do not remove any of the RBC. Add the exact amount removed of media+serum+tes. Mix gently.
Add 10 mL of the above gently mixed Babesia culture to 30 mL of 199 media/serum/tes and 3 mL RBC. Split Babesia culture 1:4.
Depending on the size of the flask use the amount of split Babesia culture necessary to maintain a viable culture.

200 mL=45 mL split Babesia culture
30 mL=15 mL split Babesia culture

Preparation of Babesia Cultures for Drug Screening
1. Make up 50 mLs Media 199+serum+tes (pH and filter).
2. Make slides of infected cultures and determine the % of infected cells.
3. Make up a 5% suspension and a 6.7% suspension or normal bovine RBC's in Media 199+serum+tes.
4. Dilute infected cells in the 6.7% suspension or normal RBC to obtain a final suspension containing 4% infected cells.

Preparation of microtiter plates.
1. Label plate as follows:
   a. Row A=200 μl 5% suspension normal RBC
   b. Row B=150 μl 4% suspension infected cells+50 μl media.
   c. Row C=150 μl 4% suspension infected cells+50 μl drug conc.
   d. Row D=150 μl 4% suspension infected cells+50 μl drug conc.
   e. Row E=150 μl 4% suspension infected cells+50 μl drug conc.
   f. Row F=150 μl 4% suspension infected cells+50 μl drug conc.
   g. Row G=150 μl 4% suspension infected cells+50 μl drug conc.
   h. Row H=150 μl 4% suspension infected cells+50 μl drug conc.
2. After plate is complete place in the incubator over night (18 hrs)
3. Add 25 μl of $^3$H hypoxanthine to each well the next morning.
4. Place the plate in the freezer at the end of the day.
5. Harvest the plate, after incubating for 2 hrs, and prepare for counting in the scintillation counter.

Preparation of Drug

1. Weight out 10 mg of drug—place in sterile 15 mL tube. Add 10 mL of media 199+serum+tes to make a concentration of 1 mg/mL or 1000 μg/mL.
Note: if not soluble use 10 mL of 70% ETOH+30% H$_2$O
2. Filter.

| | Drug Conc. | Dil factor | End Conc. in culture |
|---|---|---|---|
| a. | 1000 μg/mL | none | 150 μg/mL |
| b. | 500 μg/mL | 1:2 of a | 125 μg/mL |
| c. | 200 μg/mL | 1:5 of a | 50 μg/mL |
| d. | 100 μg/mL | 1:10 of a | 25 μg/mL |
| e. | 50 μg/mL | 1:10 of b | 12.5 μg/mL |
| f. | 20 μg/mL | 1:10 of c | 5 μg/mL |
| then dilute the 1000 μg|mL 1:50 = 20 μg/mL | | | |
| a. | 20a μg/mL | none | 5 μg/mL |
| b. | 10 μg/mL | 2:2 of a | 2.5 μg/mL |
| c. | 5 μg/mL | 1:2 of b | 1.25 μg/mL |
| d. | 2.5 μg/mL | 2:2 of c | 0.625 μg/mL |
| e. | 1.25 μg/mL | 2:2 of d | 0.31 μg/mL |
| f. | 0.625 μg/mL | 2:2 of e | 0.155 μg/mL |

Anti-*Babesia bovis* Activity

Procedure: *Babesia bovis* is maintained in in vitro culture. The cultures were diluted to a parasitemia of 4% and cultured with various dilutions of the drugs. After incubation for 18 hours 3H hypoxanthine was added and the cultures incubated for an additional 18 hours. The plates were harvested and the samples counted. Growth inhibition results in a decreased incorporation of 3H hypoxanthine. The drugs were evaluated on duplicate plates and at 2 different time intervals. With this procedure, the 50% inhibitory concentration of LL-E19020α was found to be 0.625 μg/mL.

Anti-*Babesia bigemina* Activity

Procedure: *Babesia bigemina* is maintained in in vitro culture. The cultures were diluted to a parasitemia of 4% and cultured with various dilutions of the drugs. After incubation for 18 hours 3H hypoxanthine was added and the cultures incubated for an additional 18 hours. The plates were harvested and the samples counted. Growth inhibition results in a decreased incorporation of 3H hypoxanthine can be seen in FIG. IX. The drugs were evaluated on duplicate plates and at 2 different time intervals.

EXAMPLE 4

Inoculum Preparation

A typical medium used to grow the primary inoculum was prepared according to the following formula:

| Dextrose | 1.0% |
|---|---|
| Dextrin | 2.0% |
| Yeast extract | 0.5% |
| NZ Amine A ®[1] | 0.5% |
| Calcium carbonate | 0.1% |
| Water qs | 100.0% |

[1][A pancreatic digest of casein, registered trademark of Sheffield Chemical, Norwich, NY]

This medium was adjusted to pH 7.0 and then sterilized. A 100 ml portion of this sterile medium in a 500 ml flask, was inoculated with mycelial scrapings from an agar slant of *Streptomyces lydicus* ssp. *tanzanius* NRRL 18036. The medium was then placed on a rotary shaker and incubated at 28° C. for 48 hours. This primary inoculum was then used to inoculate 10 liters of the same sterile medium in a bottle. This medium was grown for 24 hours providing secondary inoculum. This secondary inoculum was then used to inoculate 250 liters of the same sterile medium in a tank. This medium was grown at 28° C. for 48 hours with a sterile air flow of 200 liters per liter of mash per minute and agitation by an impeller driven at 220 rpm, providing tertiary inoculum.

EXAMPLE 5

Fermentation

A fermentation medium of the following formulation was prepared:

| Dextrin | 3.0% |
|---|---|
| Molasses | 2.0% |
| Soy peptone | 0.75% |
| Yeast extract | 0.25% |
| Calcium carbonate | 0.2% |
| Water qs | 100.0% |

This medium was sterilized and 2700 liters was then inoculated with 300 liters of tertiary inoculum from Example 4. The fermentation was conducted at 28° C., with a sterile air flow of 0.55 liters of air per liter of mash per minute and agitation by an impeller driven at 100 rpm for 113 hours, at which time the mash was harvested.

EXAMPLE 6

Isolation and Purification of LL-E19020α and LL-E19020β

The harvest mash from two fermentations conducted as described in Example 5 were combined, making a total of 6000 liters, adjusted to pH 5 with hydrochloric acid and filtered through diatomaceous earth. The filtrate was extracted with ethyl acetate and the extract concentrated to a syrup.

This syrup was dissolved in dichlormethane and applied to 100 g of silica (60–200 mesh) on a sintered glass funnel. The silica column was first eluted with dichloromethane, collecting four 2 liter fractions and then with methanol:dichloromethane (1:4) collecting a 4 liter fraction. This 4 liter fraction was evaporated to dryness, giving 120 g of residue. The residue was redissolved in 4 liters of dichloromethane and applied to 500 g of silica on a sintered glass funnel. The silica was eluted with methanol:dichloromethane (1:4) collecting 2 liter fractions. Fractions 1 and 2 were combined and evaporated, giving 99 g of crude LL-E19020α and β.

This crude product was dissolved in methanol and applied to a 12 liter reverse-phase column (C18 bonded phase 40 micron). The column was eluted with acetonitrile, 0.1 M ammonium acetate buffer pH 4.3 (1:1) at a rate of 1.0 liter per minute. Thirteen 24 liter fractions were collected. Fraction 7 contained LL-E19020α and fractions 11–13 contained LL-E19020β.

The antibiotics were extracted from the mobile phase using dichloromethane followed by evaporation and freeze drying from t-butanol, giving 10 g of LL-E19020α and 14 g of LL-E19020β, both as white solids.

What is claimed is:

1. A method for controlling protozoan infections in infected warm-blooded animals comprising administering to said warm-blooded animals a therapeutically effective amount of antibiotic LL-E19020α, antibiotic LL-E19020β or a pharmacologically acceptable salt thereof.

2. A method according to claim 1 wherein said warm-blooded animals are meat producing or companion animals.

3. A method according to claim 1 wherein said animals are cattle, sheep, swine, rabbits, poultry or dogs.

4. A method according to claim 1 wherein the protozoan parasite causing the infection of said warm-blooded animals is of the Eimeria or Babesia species and said antibiotic or antibiotic salt is orally administered to said warm-blooded animals in animal feed containing from about 0.1 to 300 ppm of said antibiotic or antibiotic salt.

5. A method according to claim 1 wherein the protozoan parasite causing the infection in said warm-blooded animals is of the species of the genus Eimeria or Babesia and said antibiotic is orally administered to said warm-blooded animals in sufficient amount to provide the host animal with from about 0.0001 mg/kg of animal body weight per day to about 15 mg/kg of animal body weight per day of said antibiotic or antibiotic salt.

6. A method for controlling coccidiosis in infested poultry, rabbits, cattle, swine or sheep comprising orally or parenterally administering to said infected animals a coccidicidally effective amount of an antibiotic selected from LL-E19020α, LL-E19020β and the pharmacologically acceptable salts of said antibiotics.

7. A method for controlling protozoan infections in Babesia infected cattle, sheep, dogs, or cats comprising administering to said infected animals a protozoacidally effective amount of the antibiotic LL-E19020α, LL-E19020β or a pharmacologically acceptable salt thereof.

* * * * *